United States Patent [19]

Buchel et al.

[11] 4,018,924

[45] Apr. 19, 1977

[54] PHENYL-IMIDAZOLYL-ACETAMIDE DERIVATIVES

[75] Inventors: Karl Heinz Buchel; Werner Meiser; Manfred Plempel, all of Wuppertal-Elberfeld; Carl Metzger, Dormagen, all of Germany

[73] Assignee: Bayer Aktiengesellschaft, Germany

[22] Filed: Jan. 9, 1975

[21] Appl. No.: 539,871

Related U.S. Application Data

[63] Continuation of Ser. No. 336,025, Feb. 26, 1973, abandoned, which is a continuation-in-part of Ser. No. 38,531, May 18, 1970, Pat. No. 3,732,242.

[30] Foreign Application Priority Data

May 21, 1969 Germany .......................... 1925994

[52] U.S. Cl. ........................ 424/250; 260/247.2 A; 260/268 C; 260/293.7

[51] Int. Cl.$^2$ ........................................ C07D 401/02
[58] Field of Search ................ 260/268 C; 424/250

[56] References Cited

UNITED STATES PATENTS 3,732,242   5/1973   Buchel et al. ............... 260/247.5 E

*Primary Examiner*—Donald G. Daus
*Assistant Examiner*—Jose Tovar

[57] ABSTRACT

Cyclic amides of α-phenyl-α-imidazolyl acetic acid which are further substituted by an alkyl group or phenyl group on the α-carbon atom are antimycotic agents. A typical embodiment is diphenyl imidazolyl acetic acid piperidide.

3 Claims, No Drawings

PHENYL-IMIDAZOLYL-ACETAMIDE DERIVATIVES

CROSS REFERENCE

This is a continuation of application Ser. No. 336,025, now abandoned, filed Feb. 26, 1973 which is a continuation-in-part of Ser. No. 38,531 filed May 18, 1970, now U.S. Pat. No. 3,732,242 issued May 10, 1973.

DETAILED DESCRIPTION

The present invention pertains to compounds of the formula:

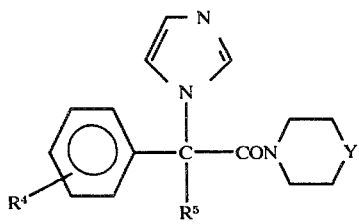

(I)

wherein
R$^4$ is hydrogen, alkyl of 1 to 4 carbon atoms, alkoxy of 1 to 4 carbon atoms, alkylmercapto of 1 to 4 carbon atoms, chloro, fluoro, bromo or nitro;
R$_5$ is alkyl of 1 to 8 carbon atoms, phenyl or phenyl substituted by alkyl of 1 to 4 carbon atoms, alkoxy of 1 to 4 carbon atoms, alkylmercapto of 1 to 4 carbon atoms, chloro, fluoro, bromo or nitro; and
Y is —CH$_2$—, O or alkylimino of 1 to 4 carbon atoms,
and the pharmaceutically acceptable nontoxic salts thereof.

The term lower alkyl denotes a univalent saturated branched or straight hydrocarbon chain containing from 1 to 4 carbon atoms. Representative of such lower alkyl groups are thus methyl, ethyl, propyl, isopropyl, butyl, isobutyl, sec.butyl and tert.butyl.

The term lower alkoxy denotes a lower alkyl chain bound to the remainder of the molecule through an ethereal oxygen atom as, for example, methoxy, ethoxy, propoxy, isopropoxy, butoxy and isobutoxy.

The term lower alkylthio denotes a lower alkyl chain bound to the remainder of the molecule through a divalent sulfur as, for example, methylthio, ethylthio, propylthio, isopropylthio, butylthio, and the like.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like. It is to be appreciated that while the salt emmbodiments of the present invention may be more convenient in handling, the activity of these salts is a function of the cation.

The compounds of the present invention are prepared by allowing a haloacetamide of the formula:

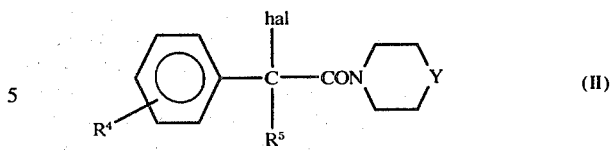

(II)

wherein R$^4$, R$^5$ and Y are as herein defined and "hal" is chloro or bromo to react (a.) with imidazole in the presence of an acid binding agent, which can be excess imidazole, in an inert polar organic solvent such as acetonitrile, toluene, xylene, chlorobenzene, cyclohexane, acetone, diethylketone, dimethylformamide, dimethylsulfoxide or the like at temperatures of from 20° to 180° C, preferably 50° to 100° C, or (b.) with an alkali metal or silver salt of imidazole in an inert polar organic solvent at temperatures of from about 20° to about 200° C, preferably 50° to 120° C. The compounds are produced directly, can be isolated by conventional techniques such as removal of any solvent by distillation, and can be purified as through recrystallization. Salts are prepared by treatment with the appropriate acid in one or more nonaqueous solvents.

The above chloroacetamides of Formula II are known or can be produced by well known methods, as for example the reaction of the appropriately substituted phenyl chloroacetyl chloride and the cyclic amine. (See Ber. 22, 1537).

When R$^5$ is different from the depicted phenyl group, the amides of Formula I will exist as optical isomers and both the racemates of these isomers and the individual isomers themselves are within the scope of the present invention. The racemates are generally completely satisfactory for the intended use but can be separated into their individual isomers through the well known technique such as formation of diastereoisomeric salts with optically active acids.

The cyclic amides of the present invention and their salts are useful in combatting dermatoses caused by fungi such as Trichophytes, Microsporium, Epidermophytes, Aspergillus, Candida and the like, as well as organomycoses caused by yeasts, mould fungi and Dermatophytes.

Particularly preferred compounds are those of the formula:

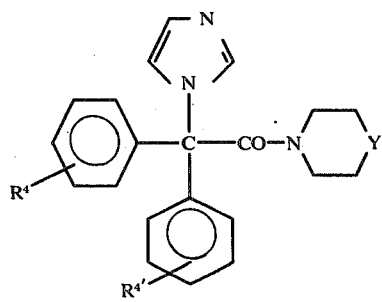

wherein each of R$^4$ and R$^{4'}$, independent of the other, is hydrogen, methyl, methoxy, methylmercapto, chloro, fluoro, bromo or nitro and
Y is —CH$_2$—, >NCH$_3$ or —O—.

The present invention also comprises pharmaceutical compositions which contain a major or minor amount, e.g. from 95 to 0.5%, of at least one cyclic amide as herein defined in combination with a pharmaceutical carrier, the carrier comprising one or more solid, semisolid or liquid diluent, filler and formulation adjuvant which is nontoxic, indert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 20 mg/kg to about 50 mg/kg. In some instances a sufficient therapeutic effect can be obtained at a lower dose while in others, a larger dose will be required.

Oral administration can be effected utilizing solid and liquid dosage unit forms such as powders, tablets, dragees, capsules granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellant such as the chlorofluorohydrocarbons.

The following examples present a number of typical embodiments of the present invention. Since other compounds of this invention are prepared in a completely analogous fashion from the correspondingly substituted compounds, the following examples are believed to be sufficiently full, clear, concise and exact to permit practice of the invention, which invention is defined solely by the appended claims.

EXAMPLE 1

A mixture of 15.5 g of diphenylchloroacetic acid morpholide, m.p. 113° C (prepared from diphenylchloroacetyl chloride and morpholine in accordance with the procedure described in Ber. 41, 3593) and 11g of imidazole in 100 ml of acetonitrile is heated at reflux for 18 hours. The solvent is removed by distillation in vacuo and, after addition of 70 ml of water, the residue is extracted with methylene chloride. The extracts are dried and the solvent is removed by distillation to yield diphenyl-imidazolylacetic acid morpholide which is further purified by recrystallization from methanol. The hydrochloride salt, m.p. 118° C, is obtained by treating an ethyl acetate solution of the free base with an ethereal solution of hydrogen chloride.

In a similar fashion from the corresponding amounts of phenyl-(2-methylphenyl)chloroacetic acid morpholide; phenyl-(2-methoxyphenyl)chloroacetic acid morpholide, bis(4-chlorophenyl)-chloroacetic acid morpholide, phenyl-(2-methylmercaptophenyl)-chloroacetic acid morpholide, bis-(4-nitrophenyl)chloroacetic acid morpholide and phenyl-t-butylchloroacetic acid morpholide, there are respectively obtained, phenyl-(2-methylphenyl)imidazolylacetic acid morpholide; phenyl-(2-methoxyphenyl)imidazolylacetic acid morpholide; bis-(4-chlorophenyl)imidazolylacetic acid morpholide; phenyl-(2-methylmercaptophenyl)imidazolylacetic acid morpholide; bis-(4-nitrophenyl)imidazolylacetic acid morpholide and phenyl-t-butylimidazolylacetic acid morpholide.

EXAMPLE 2

In a similar fashion to that described in Example 1, diphenylimidazolylacetic acid piperidide, m.p. 160° C, is obtained from 15.4 g of diphenylchloroacetic acid piperidide, m.p. 82° C., and 10 g of imidazole in 100 ml of acetonitrile.

Similarly prepared is bis(4-bromophenyl)imidazolylacetic acid piperidide.

EXAMPLE 3

Utilization of equivalent amounts of diphenylchloroacetic acid N'-methylpiperazide, bis-(4-chlorophenyl)chloroacetic acid N'-methylpiperazide and bis-(2-chlorophenyl)chloroacetic acid N'-methylpiperazide in the procedure of Example 1 yields diphenylimidazolylacetic acid N'-methylpiperazide, m.p. 173° C; bis-(4-chlorophenyl)imidazolylacetic acid N'-methylpiperazide, m.p. 166°–169° C; and bis-(2-chlorophenyl)imidazolylacetic acid N'-methylpiperazide, m.p. 158°–160° C.

What is claimed is:

1. The compound of the formula:

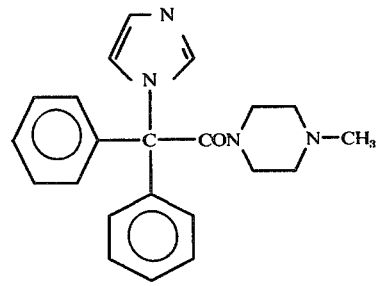

or a pharmaceutically acceptable nontoxic salt thereof.

2. A pharmaceutical composition useful for treating mycotic infections in humans and animals which comprises an antimycotically effective amount of the compound of claim 1 or a pharmaceutically acceptable nontoxic salt thereof in combination with a pharmaceutically acceptable nontoxic inert diluent or carrier.

3. A method of treating mycotic infections in humans and animals which comprises administering to said human or animal an antimycotically effective amount of the compound of claim 1 or a pharmaceutically acceptable nontoxic salt thereof.

* * * * *